US008230852B2

(12) United States Patent
Zhang et al.

(10) Patent No.: US 8,230,852 B2
(45) Date of Patent: Jul. 31, 2012

(54) SHOULDER MOUNTED HOOD COOLING SYSTEM

(75) Inventors: Yajun-Edwin Zhang, Shanghai (CN); Zhao Xia Jin, Shanghai (CN); Mike Berg, Carol Stream, IL (US)

(73) Assignee: Honeywell International Inc., Morristown, NJ (US)

( * ) Notice: Subject to any disclaimer, the term of this patent is extended or adjusted under 35 U.S.C. 154(b) by 105 days.

(21) Appl. No.: 12/790,397

(22) Filed: May 28, 2010

(65) Prior Publication Data

US 2011/0289954 A1 Dec. 1, 2011

(51) Int. Cl.
*A61M 16/00* (2006.01)
*A62B 17/00* (2006.01)
*A61B 18/00* (2006.01)

(52) U.S. Cl. ......... 128/201.22; 128/201.23; 128/201.29; 128/204.15; 128/204.18; 128/200.28; 2/459; 2/460; 2/461; 2/462

(58) Field of Classification Search ............. 128/200.24, 128/201.22, 201.23, 201.27, 202.11, 202.19, 128/204.18, 204.21; 2/421, 456, 459, 460, 2/461, 462
See application file for complete search history.

(56) References Cited

U.S. PATENT DOCUMENTS 2,171,337 A * 8/1939 Hellmann et al. ....... 128/201.29
3,049,896 A * 8/1962 Webb ....................... 128/201.25
3,525,334 A * 8/1970 Braman et al. ........... 128/201.25
4,019,508 A * 4/1977 Der Estephanian et al. ........................ 128/202.19
4,158,242 A * 6/1979 Mitchell ........................... 2/462
5,265,592 A * 11/1993 Beaussant ................ 128/201.24
H1360 H * 10/1994 Grove et al. ............. 128/201.25
5,655,374 A * 8/1997 Santilli et al. ..................... 62/3.5
6,401,715 B1 * 6/2002 Luthe ....................... 128/205.28
7,357,135 B2 4/2008 Cunningham et al.
7,516,743 B2 * 4/2009 Hoffman .................. 128/204.23
2007/0095344 A1 * 5/2007 Abernethy ............... 128/202.12
2007/0163600 A1 7/2007 Hoffman
2008/0295220 A1 12/2008 Webb

FOREIGN PATENT DOCUMENTS

CH 556 664 12/1974
EP 0 490 347 A1 6/1992
EP 0 791 301 A2 8/1997

OTHER PUBLICATIONS

European Search Report corresponding to Application No. EP 11 16 6615, mailed Oct. 6, 2011.
Data supplied by Espacenet's database indicating that abstract is not available for CH556664 (A).
English translation of CH 556 664.

* cited by examiner

*Primary Examiner* — Clinton T Ostrup
(74) *Attorney, Agent, or Firm* — Husch Blackwell LLP

(57) ABSTRACT

A shoulder mounted hood cooling assembly includes a support, a blower carried by the support, and vents in fluid communication with the blower. The support when worn by a user positions at least a portion of the support adjacent the user's shoulder's and the vents are positioned to direct air exhausted from the blower to a neck or to a head or both the neck and the head of the user.

11 Claims, 8 Drawing Sheets

SHOULDER MOUNTED HOOD COOLING SYSTEM

FIELD OF INVENTION

The present invention concerns a shoulder mounted hood cooling assembly. The assembly includes a blower support and a blower unit. The blower support includes shoulder mounts which rest on the shoulder of a user.

BACKGROUND

Workers are required to wear an arc protection hood to protect against the potentially devastating affects of arc flash.

U.S. Patent Publication 2008/0295220, Fan-based Cooler for Head-Protection Gear, Webb, discloses a cooler accessory with a hard hat or other head protecting gear having a protective shell with a rim. The accessory includes a housing that is attachable to the protective shell. Tubing extends from the housing. Air flow supply means in the housing supplies a flow of air that passes through the tubing and exits therefrom. During use, the tubing extends below the rim of the protective shelf for directing the flow of air supplied by the airflow supply means under the rim for injection towards a space adjacent the user's body thereby cooling the user's body. Preferably the tubing is configured such that the air flow is injected into an air gap between the user's head and the protective shell and over the user's head, thereby actively cooling the user's head. The accessory's housing can be removably secured to the protective shell by many different ways including adhesive means, straps, clips, a slotted interface or other suitable fixation mechanisms.

U.S. Pat. No. 7,357,135, Protective Hood with Fan Assembly, Cunningham, discloses a protective hood with a vent opening and a transparent shield mounted to a front portion of the hood. In a basic configuration a fan assembly is removably mounted to the hood and coupled to the vent opening to direct air flow within the hood. In another configuration a fan assembly is selectively attachable to the vent opening or position. Optionally a rear flap selectively seals the vent position when the fan assembly is not attached and the rear flap partially covers a fan when the fan assembly is attached to the hood.

SUMMARY

The present disclosure concerns a shoulder mounted hood cooling assembly which includes a support, a blower carried by the support, and vents in fluid communication with the blower. When a user wears the support at least a portion of the support is adjacent the user's shoulder's and the vents are positioned to direct air exhausted from the blower to a neck or to a head or both the neck and the head of the user.

In more detail the support can include a first curved shoulder mount forming a portion of the support. The first shoulder mount defines an inwardly facing side surface. Additionally, a second curved shoulder mount forms a portion of the support. The second shoulder mount defines a inwardly facing side surface. A first chest portion extends downward from the first curved shoulder support and at a front of the support. The first chest portion defines an inwardly facing side surface. A second chest portion extends downward from the second curved shoulder mount and at a front of the support. The second chest portion defines an inwardly facing side surface. A back portion extends downward from said first and second shoulder mounts at the back of the support. The back portion defines an inwardly facing side surface. A neck accommodating space is defined by the inwardly facing side surfaces.

When the support is worn by a user, the shoulder mounts rest on top of the user's shoulders. The vents open through one of the side surfaces.

DETAILED DESCRIPTION

Figure 1:
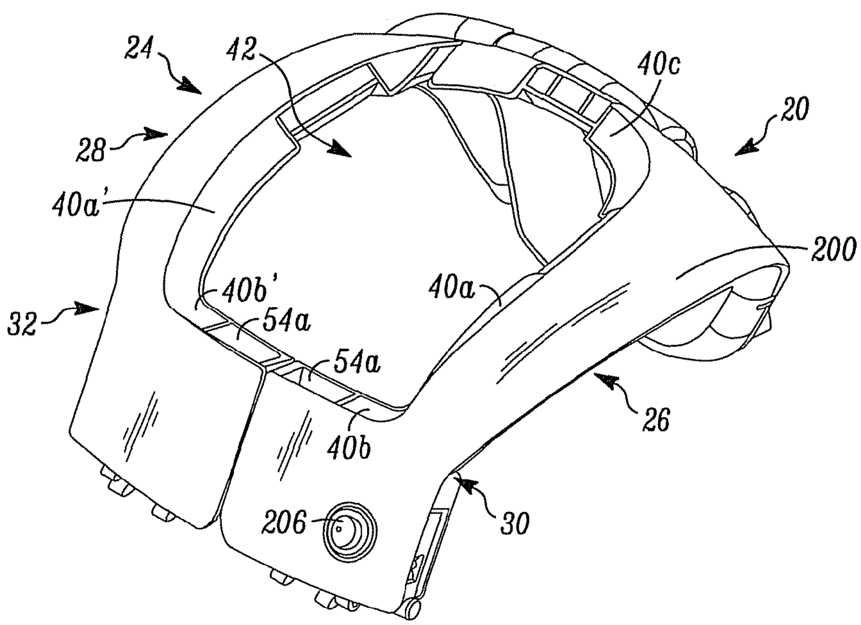
FIG. 1 is an isometric front view of a shoulder mounted hood cooling assembly embodying the features of my invention.
Figure 2:
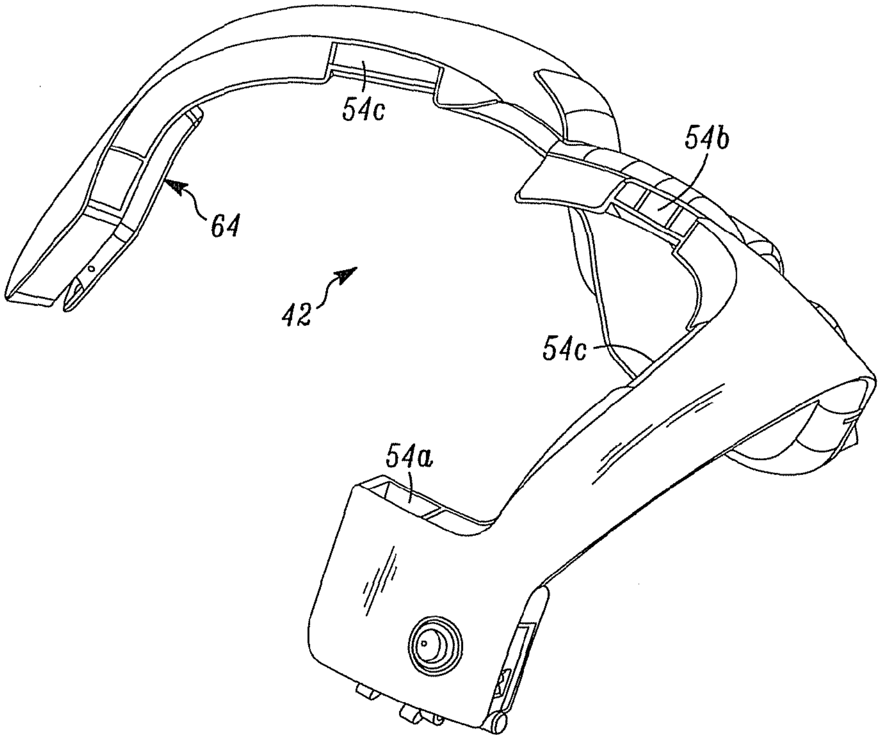
FIG. 2 is an isometric front view of the assembly of FIG. 1 shown in an open position.
Figure 3:
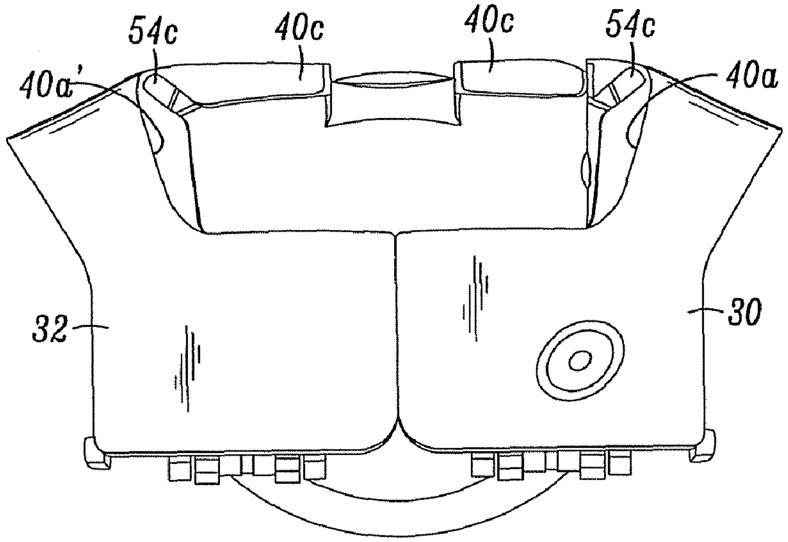
FIG. 3 is a front view of the assembly shown in FIG. 1.
Figure 4:
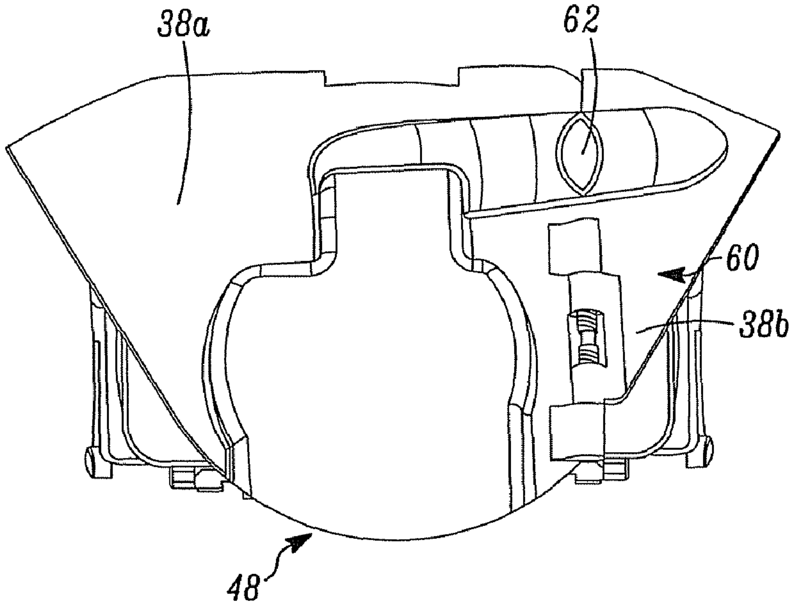
FIG. 4 is a back view of the assembly shown in FIG. 1.

FIGS. 1-9 disclose a shoulder mounted hood cooling assembly 20. The assembly includes a blower 22 carried by a blower support 24. The blower support 24 is adapted to be carried by the shoulders of a user 34 when in use.

The blower support includes two curved shoulder mounts 26, 28. The mounts rest on top of a user's shoulders when in use. Extending downward from each mount, at the front of the support, are chest portions 30, 32. The chest portions 30, 32 which can also be referred to as chest abutments are located at the user's upper torso in an area adjacent the user's chest when the support is worn. The chest portions 30, 32 when around a user are coupled together by way of fasteners 36 such as magnets. The chest portions together form a chest mount or plate.

The blower support includes a back portion, mount, or plate extending downward from the shoulder mounts at the back of the support. The back portion is made up of a first back portion 38*a* and a second back portion 38*b*. The back portion is located adjacent the user's upper back and shoulder blade area when the support is worn by the user. The shoulder mounts 26, 28, chest portions 30, 32, and back portion 38*a*, 38*b* each have inwardly facing side surfaces 40*a*, 40*a*'; 40*b*, 40*b*'; 40*c* which together define a neck accommodating space 42. A user's neck is in the space when the support is worn by the user.

Figure 5:
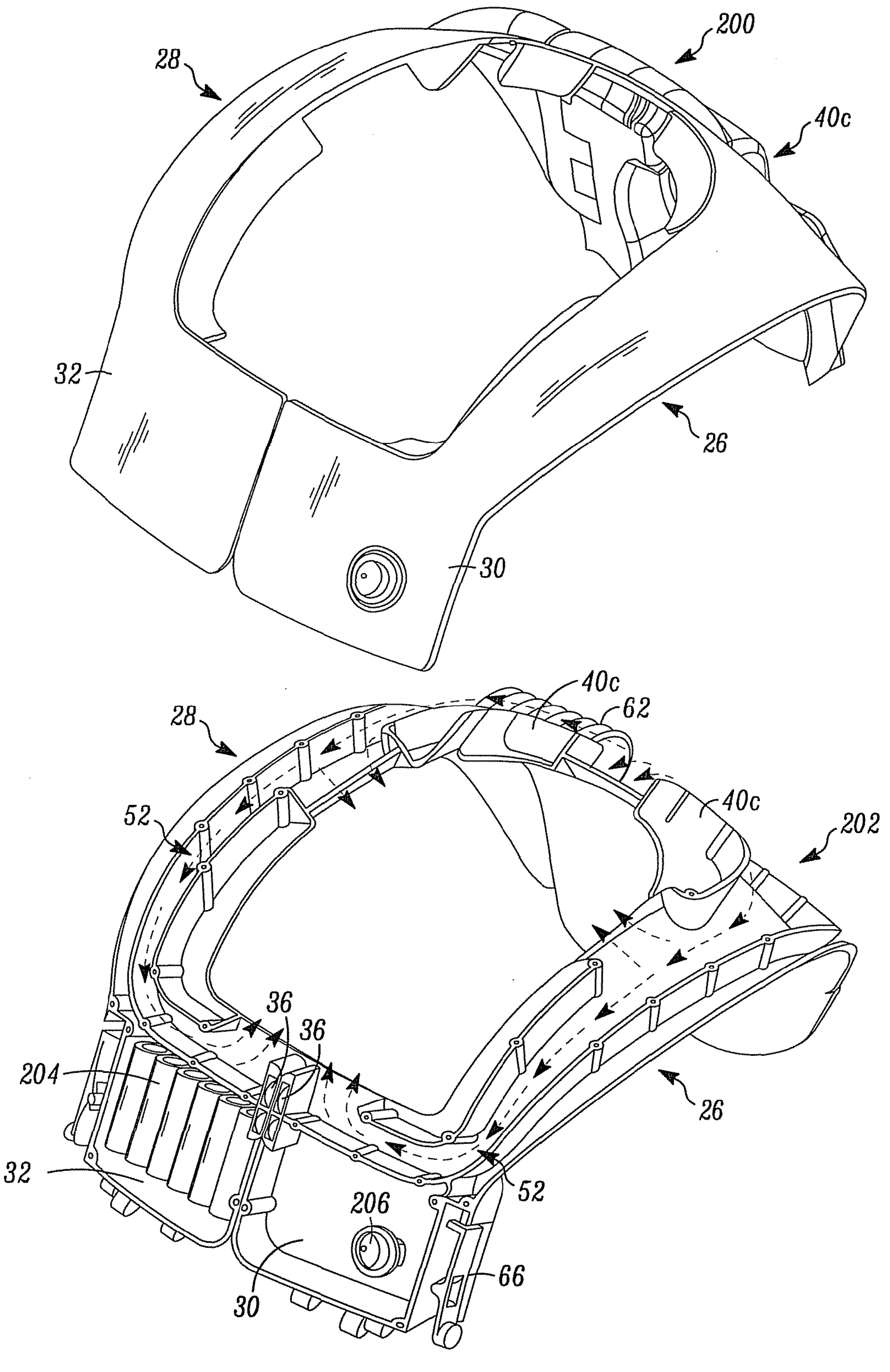
FIG. 5 is an exploded isometric front view of the assembly shown in FIG. 1 with the upper shell removed to show the internal passages and ducts formed in the support of the assembly; the dashed lines show air flow in and out of the support.
Figure 6:
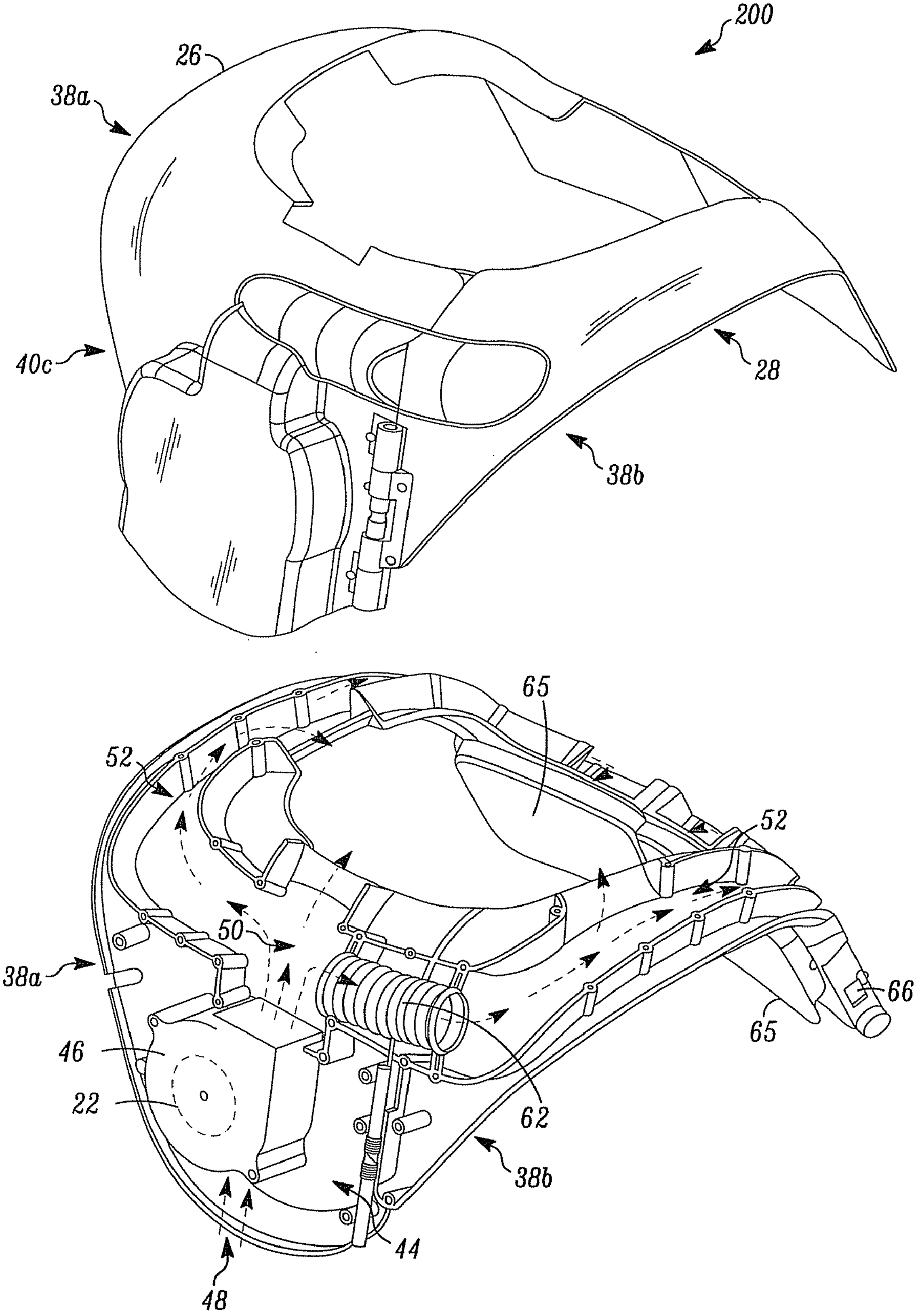
FIG. 6 is a back isometric view of the structure shown in FIG. 5; the dashed lines show airflow in and out of the support.
Figure 9:
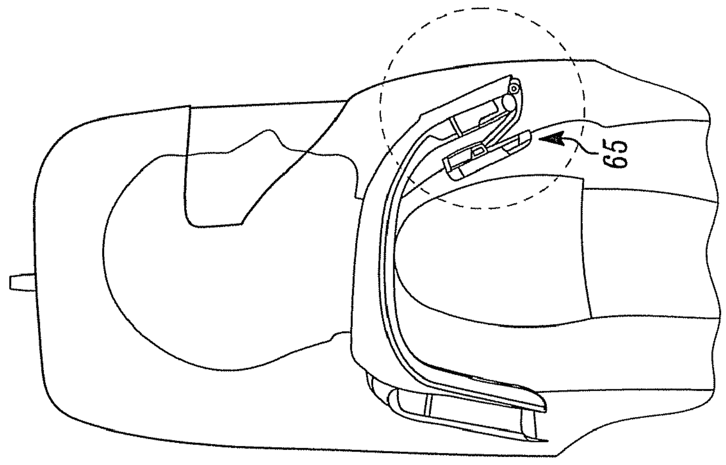
FIG. 9 is the same side view shown in FIG. 8 except the abutment has been deployed.
Figure 8:
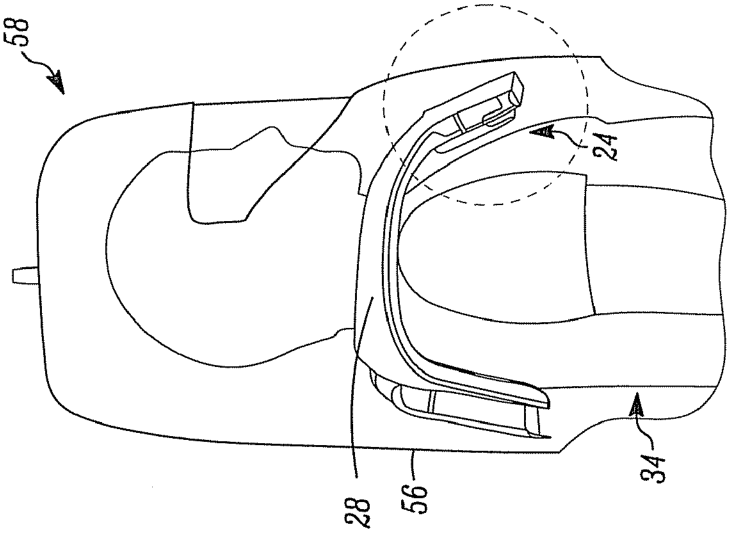
FIG. 8 is a side view of the person in FIG. 7 wearing the assembly and hood; the assembly has its abutment in the locked position.
Figure 7:
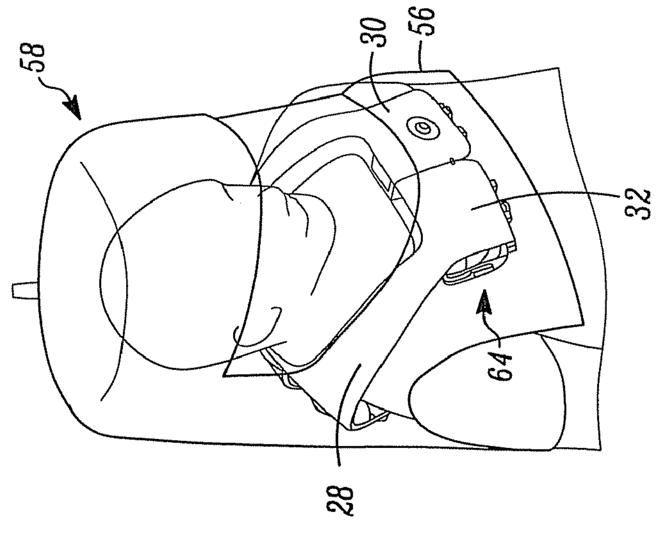
FIG. 7 is a front isometric view of the assembly as worn by a person when the users is wearing an arc protection hood.

The back plate 38*a*, 38*b* has a portion which defines an internal hollow 44 in which a blower is carried. The blower 22 itself is in a blower housing 46 which is in the hollow 44. The back plate or portion has an inlet 48 which leads into the hollow 44. The inlet allows air to be drawn into the blower housing 46. The back portion has an internal passage 50 leading from the hollow which directs air being exhausted from the blower to a system of internal ducts 52 formed by the blower support. The ducts lead to vents 54*a*, 54*b*, 54*c* in the side surfaces defining the neck opening. The vents exhaust air towards a user's head and neck. The hollow, passage, ducts and vents are formed between support base 202 and support shell 200. FIGS. 5, 6 shows the shell 200 removed from the base 202. The FIGS. 5, 6 help show the location of the hollow, passage, ducts and vents.

The support when resting on the shoulder's of a user positions the vents so that a drape 56 of a protective hood 58 falls over and beyond the vents. Air exiting the vents is confined by the drape and forced into open space between the hood and the user's neck and head. The vents 54*a* in the chest portion's side surfaces direct air at the user's face and front neck. The vent in the back portion 54*b* directs air at the back neck and back of the head. The vents 54*c* in the shoulder mounts direct air to each lateral side of the neck and head.

It is also possible that the blower does not have a housing distinct from the portion of the back plate which forms the hollow. The blower would be mounted within the hollow 44 without its housing. The back plate inlet 48, hollow 44 and passage 50 would direct the air to and from the blower. The blower in this case is an impeller. The blower could be any air conveyor such as a rotatary vane, piston, screw or claw.

To facilitate the user's ability to put on the support, the support is hinged. The hinge 60 joins a first portion of the support to a second portion. The first portion of the support includes first shoulder mount, 26 first chest portion 30 extending from the first shoulder mount, and first back portion 38*a* of the extending from the first shoulder mount. The second portion of the support includes second shoulder mount 28 second chest portion 32 extending from the second shoulder mount and second back portion 38*b* extending from the second shoulder mount. The hinge joins the first and second support portions together at the first 38*a* and second 38*b* back portions.

Having the portions hinged together allows a user to separate the first shoulder mount 26 and first chest portion 30 from the second shoulder mount 28 and second chest portion 32 in the lateral direction. The separation increases the size of the neck accommodating space making it easier for the user to install the support on the user's body.

A flexible tube 62 joins a first portion of the passage 50 in the first back portion 38*a* to a second portion of the passage 50 in the second back portion 38*b*. The tube helps ensure no air leaks from the passage.

To improve fit on a user, the support has adjustable abutment assemblies 64. Each chest portion, on its internal side, carries an adjustable abutment assembly 64. The abutment 65 of each assembly is spring loaded so when the spring member is in an uncompressed state, the abutment is spaced a maximum distance from chest portions towards the back portion.

The spring loaded spacing means the abutment will move from back to front of the support depending on the size of a user's chest. A user with a big chest will push the abutment more towards the front than a user with a small chest.

A lock mechanism allows a user to lock the abutment at the front of the support.

The support is constructed so that it retains it shape when not in use. The support is made of material which includes hard plastic. The external surface 200 of the support and base 202 are made of hard plastic. Shell 200 is made up of a first seamless monolithic piece of plastic and a second seamless monolithic piece of plastic joined to the first piece with hinge 60. Base 202 is made up of a first seamless piece of monolithic plastic and a second piece of monolithic plastic. Each piece is joined to the other by hinge 60. The hard plastic defines the ducts, passage, and hollow. To maintain its shape the support needs to be at least framed by a hard material such as hard plastic. Padding can line the interior of at least some of the base 202 for comfort.

One of the chest portions carry a switch 206 which allows a user to turn the blower on and off. Another of the chest portions carries batteries 204 which power the blower. Accordingly, the batteries 204 and switch 206 are electronically coupled to a motor which powers the blower. A charge port 66 can be disposed on the support. The charge port 66 is electrically coupled to the batteries 204 and/or the switch 206.

The support can include straps extending from the chest portions and from the back plate. The straps allow a user to further secure the support to their body during use.

Figure 10A:
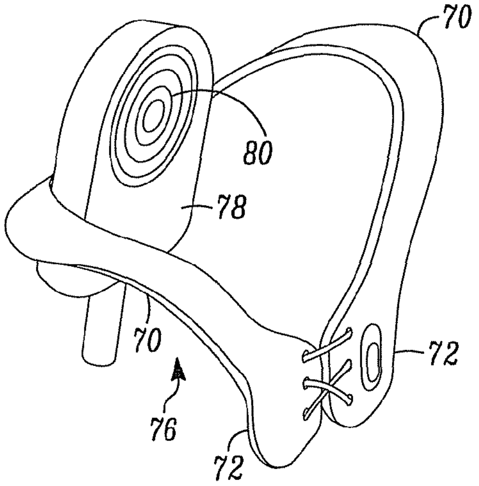
FIGS. 10*a* and 10*b* show an alternative embodiment of a shoulder mounted hood cooling assembly embodying my invention.
Figure 10B:
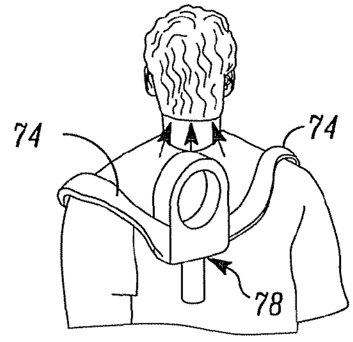

FIGS. 10*a*, 10*b*; 11*a*, 11*b*; 12; and 13 show more basic examples of a shoulder mounted hood cooling assembly. All of the supports shown in these figures have shoulder mounts 70 chest portions 72 and a back portion 74. These features are clearly shown in FIGS. 10*a* and 10*b*. The supports do not have an internal hollow housing the blower or a system of internal ducts with vents to direct air to the user's neck and head.

The support 76 in FIGS. 10*a*, 10*b* carries a blower and blower housing 78 at the support's back portion. The housing has vents 80 to direct air to the back of the neck.

Figure 11A:
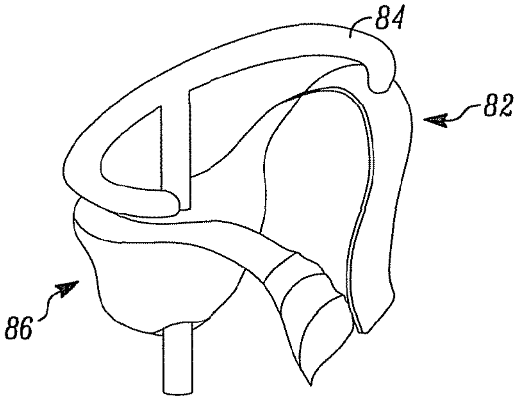
FIGS. 11*a* and 11*b* are of a third embodiment of my invention showing a shoulder mounted hood cooling assembly with vent tubes to direct air around a users head.
Figure 11B:
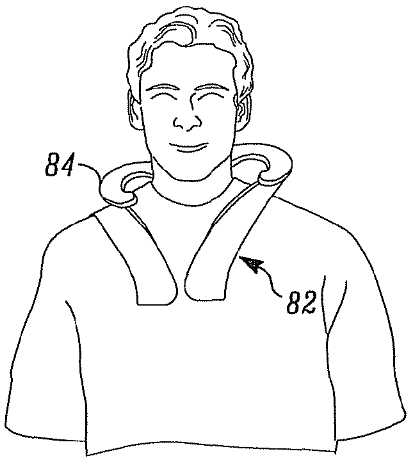

The support 82 in FIGS. 11*a*, 11*b* carries a blower and blower housing 86 at its back portion with vent tubes 84 extending from the blower housing to direct air around a user's head.

Figure 12:
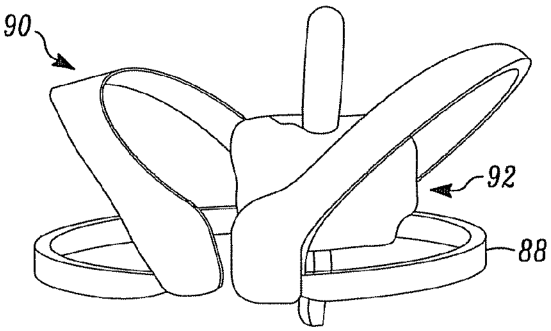
FIG. 12 is a fourth embodiment of my invention showing a shoulder mounted hood cooling assembly with a horizontal torso strap.

The support 90 of FIG. 12 includes a horizontal torso strap 88 to help secure the support to the user. The support 90 carries the blower and blower housing 92 at its back portion.

Figure 13:
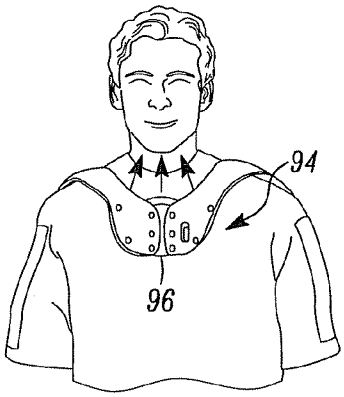
FIG. 13 is a fifth embodiment of my invention showing a shoulder mounted assembly; the assembly has the blower mounted to a front of the support.

FIG. 13 shows a support 94 which carries a blower and blower housing 96 at the supports front portion.

Figure 14A:
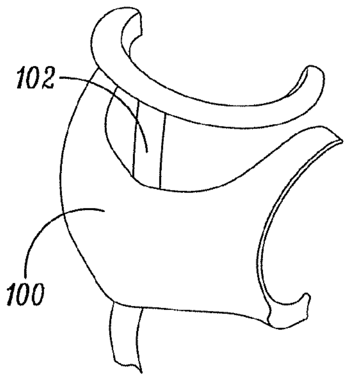
FIGS. 14*a* and 14*b* are a sixth embodiment of my invention showing a support with straps carrying a bag at the back; the bag carries a blower assembly.
Figure 14B:
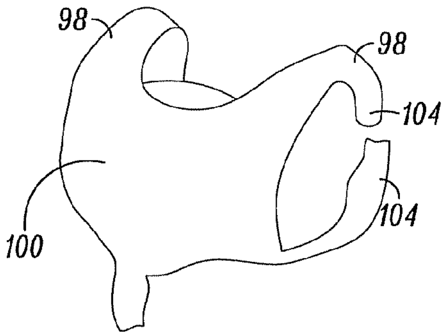

FIGS. 14*a*, 14*b* show a support with two shoulder straps 98 carrying a bag 100 at the back. The back carries blower assembly 102. Each of the two straps 98 includes first and second strap portions which are fastened together by fasteners such as VELCRO® fasteners 104.

Figure 15A:
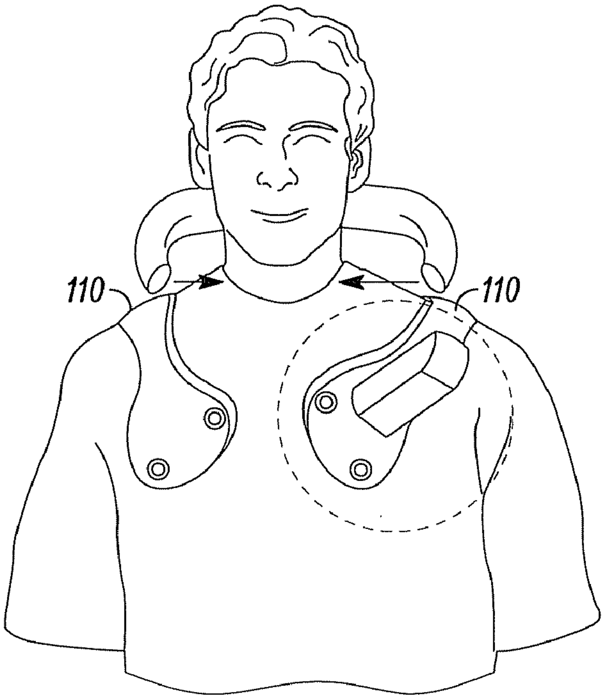
FIGS. 15*a* and 15*b* are a seventh embodiment of my invention showing a support with a blower assembly at its back; the supports back and front are pinned to the user; the front carries a battery and switch for the blower.
Figure 15B:
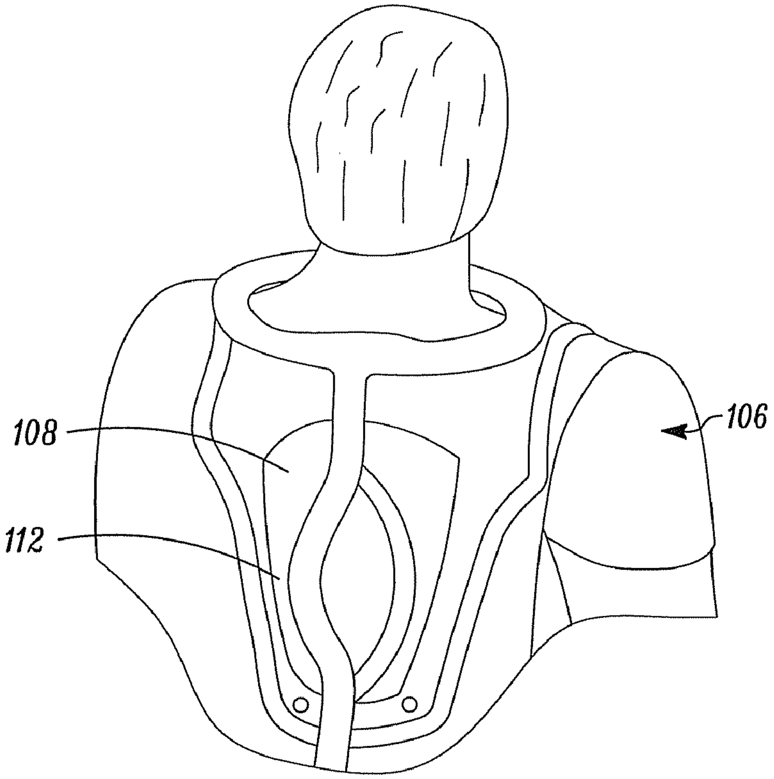

FIGS. 15*a*, 15*b* show a fabric crushable support 106 carrying a blower assembly 112 at its back portion. The back portion 108 is pinned to a user's clothing. The shoulder mounts 110 extend from the back portion and are pinned to the user's clothing.

The term user encompasses an adult male or female around the age of 40 with an average build.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

Although an example of the invention has been disclosed, it will be appreciated by those skilled in the art that various changes and modifications might be made without departing from the spirit and scope of the invention.

The invention claimed is:

1. A shoulder mounted hood cooling assembly comprising:

a support having a base and a shell;

a blower carried between said base and said shell of said support;

a first curved shoulder mount forming a portion of said base and said shell of said support, said first curved shoulder mount defining an inwardly facing side surface;

a second curved shoulder mount forming a portion of said base and said shell of said support, said second curved shoulder mount defining an inwardly facing side surface;

a first chest portion extending downward from said first curved shoulder mount and at a front of said base and said shell of said support, said first chest portion defining an inwardly facing side surface;

a second chest portion extending downward from second said curved shoulder mount and at a front of said base and said shell of said support, said second chest portion defining an inwardly facing side surface;

a back portion extending downward from said first and second curved shoulder mounts at the back of said base and said shell of said support, said back portion defining an inwardly facing side surface;

a neck accommodating space defined by each of said inwardly facing side surfaces;

an internal passage carried between said base and said shell of said support, said internal passage in fluid communication with said blower;

a system of internal ducts carried between said base and said shell of said support, said system of internal ducts in fluid communication with said internal passage; and a plurality of vents formed in respective ones of said inwardly facing side surfaces, said plurality of vents in fluid communication with said system of internal ducts, wherein said blower draws air therein, said internal passage directs the air from said blower to said system of internal ducts, said system of internal ducts directs the air from said internal passage to said plurality of vents, and said plurality of vents exhausts the air, wherein when said support is worn by a user, each of the first and second curved shoulder mounts rests on top of the user's shoulders and the support positions the plurality of vents to exhaust the air towards a neck, a head, or both the neck and the head of the user, and wherein the air traveling between said blower, said internal passage, said system of internal ducts, and said plurality of vents is contained and directed by said base and said shell of said support until said plurality of vents exhaust the air.

2. The shoulder mounted cooling assembly of claim 1 wherein said each of said plurality of vents opens through one of said inwardly facing side surfaces.

3. The shoulder mounted hood cooling assembly of claim 1 further comprising:

an internal hollow formed between said base and said shell of said support, said blower in said internal hollow.

4. The shoulder mounted hood cooling assembly of claim 3 wherein said internal passage is in fluid communication with said internal hollow.

5. The shoulder mounted hood cooling assembly of claim 4 wherein said blower itself is in a housing distinct from said base and said shell of said support.

6. The shoulder mounted hood cooling assembly of claim 1 further comprising:

a hinge joining a first portion of the support to a second portion of the support.

7. The shoulder mounted hood cooling assembly of claim 6 wherein said first portion of the support includes said first curved shoulder mount, said first chest portion and a first portion of said back portion and wherein said second portion of the support includes said second curved shoulder mount, said second chest portion and a second back portion of said back portion.

8. The shoulder mounted hood cooling assembly of claim 7 wherein said hinge joins the first and second support portions together at the first and second back portions.

9. The shoulder mounted hood cooling assembly of claim 1 further comprising an adjustable abutment assembly on an internal side of said first chest portion, said adjustable abutment assembly having an abutment movable from back to front and from front to back of the support.

10. The shoulder mounted hood cooling assembly of claim 9 having a lock mechanism to lock the abutment assembly so the abutment will be locked in a position at the front of the support.

11. The shoulder mounted hood cooling assembly of claim 1 wherein said shell of said support includes a seamless monolithic shell or said base of said support includes a seamless monolithic base.

* * * * *